(12) United States Patent
Takato et al.

(10) Patent No.: US 10,130,245 B2
(45) Date of Patent: Nov. 20, 2018

(54) ENDOSCOPE APPARATUS

(71) Applicant: OLYMPUS CORPORATION, Tokyo (JP)

(72) Inventors: Hideyasu Takato, Tokyo (JP); Nobuhiko Sone, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/159,293

(22) Filed: May 19, 2016

(65) Prior Publication Data

US 2016/0256042 A1 Sep. 8, 2016

Related U.S. Application Data

(63) Continuation of application No. PCT/JP2014/084164, filed on Dec. 24, 2014.

(30) Foreign Application Priority Data

Jan. 15, 2014 (JP) .................................. 2014-005132

(51) Int. Cl.
*A61B 1/06* (2006.01)
*G02B 23/26* (2006.01)
*A61B 1/07* (2006.01)

(52) U.S. Cl.
CPC .......... *A61B 1/0623* (2013.01); *A61B 1/0638* (2013.01); *A61B 1/0676* (2013.01); *A61B 1/07* (2013.01); *G02B 23/26* (2013.01)

(58) Field of Classification Search
CPC ..... A61B 1/0623; A61B 1/00096; A61B 1/06; G02B 23/26

(Continued)

(56) References Cited

U.S. PATENT DOCUMENTS 4,660,982 A * 4/1987 Okada ................ A61B 1/00096
356/636
4,787,370 A * 11/1988 Kanamori .......... A61B 1/00101
600/170

(Continued)

FOREIGN PATENT DOCUMENTS

JP 11-076151 3/1999
JP 2000-37345 2/2000

(Continued)

OTHER PUBLICATIONS

International Search Report, mailed Mar. 24, 2015, issued in corresponding International Application No. PCT/JP2014/084164.

*Primary Examiner* — Anhtuan T Nguyen
*Assistant Examiner* — Jae Woo
(74) *Attorney, Agent, or Firm* — Hunton Andrews Kurth LLP

(57) ABSTRACT

In order to perform a superior observation, in which halation is less likely to occur, by achieving uniform illumination from near sites to far sites and by ensuring a satisfactory light distribution and brightness, both when performing normal observation and when performing near-field observation, an endoscope apparatus includes an observation optical system that is provided at a distal end of an inserted portion of the endoscope apparatus to observe an observation subject and a plurality of illumination optical systems that are provided in the inserted portion and that illuminate the same viewing field by distributing illumination light emitted from a light source over the observation subject, wherein, of the plurality of the illumination optical systems, the distance from the observation optical system to the widest-angle illumination optical system is smaller than the distance from the observation optical system to the narrowest-angle illumination optical system.

8 Claims, 9 Drawing Sheets

(58) Field of Classification Search
USPC ........ 600/177, 176, 117, 182; 359/707, 718; 385/119, 117
See application file for complete search history.

(56) References Cited

U.S. PATENT DOCUMENTS

| | | | | |
|---|---|---|---|---|
| 4,952,040 | A * | 8/1990 | Igarashi | G02B 23/2469 359/708 |
| 5,966,168 | A * | 10/1999 | Miyazaki | A61B 1/00096 348/68 |
| 9,039,605 | B2 * | 5/2015 | Sone | A61B 1/00096 600/117 |
| 2001/0003142 | A1 * | 6/2001 | Koshikawa | A61B 1/00096 600/177 |
| 2004/0057108 | A1 * | 3/2004 | Namii | G02B 21/0012 359/385 |
| 2006/0018031 | A1 * | 1/2006 | Takasugi | G02B 6/0006 359/661 |
| 2006/0052668 | A1 * | 3/2006 | Homma | A61B 1/07 600/177 |
| 2007/0049803 | A1 * | 3/2007 | Moriyama | A61B 1/00096 600/176 |
| 2007/0100200 | A1 * | 5/2007 | Suzuki | A61B 1/00151 600/101 |
| 2008/0045797 | A1 * | 2/2008 | Yasushi | A61B 1/00096 600/175 |
| 2009/0009759 | A1 * | 1/2009 | Backman | A61B 1/00096 356/303 |
| 2010/0312057 | A1 * | 12/2010 | Konno | A61B 1/00177 600/162 |
| 2011/0157574 | A1 * | 6/2011 | Kato | A61B 1/05 355/71 |
| 2011/0261178 | A1 * | 10/2011 | Lo | A61B 1/05 348/68 |
| 2012/0232343 | A1 * | 9/2012 | Levy | A61B 1/00177 600/109 |
| 2012/0245421 | A1 * | 9/2012 | Kitano | A61B 1/00039 600/180 |
| 2013/0310649 | A1 * | 11/2013 | Sone | A61B 1/00096 600/177 |
| 2014/0081085 | A1 * | 3/2014 | Takato | A61B 1/00096 600/129 |
| 2014/0330078 | A1 * | 11/2014 | Hwang | A61B 1/00193 600/111 |
| 2015/0092035 | A1 * | 4/2015 | Yamamoto | G02B 21/06 348/68 |
| 2015/0257630 | A1 * | 9/2015 | Sone | A61B 1/00 600/109 |
| 2015/0320300 | A1 * | 11/2015 | Gershov | A61B 1/045 600/109 |
| 2015/0359422 | A1 * | 12/2015 | Igarashi | G02B 23/243 600/135 |
| 2016/0015258 | A1 * | 1/2016 | Levin | A61B 1/00006 600/109 |
| 2016/0106306 | A1 * | 4/2016 | Furuta | A61B 1/00163 600/176 |
| 2016/0150944 | A1 * | 6/2016 | Tearney | A61B 1/00016 600/109 |
| 2016/0256042 | A1 * | 9/2016 | Takato | G02B 23/26 |
| 2016/0345811 | A1 * | 12/2016 | Sone | A61B 1/00 |

FOREIGN PATENT DOCUMENTS

| | | |
|---|---|---|
| JP | 2001-166223 | 6/2001 |
| JP | 2001-346752 | 12/2001 |
| JP | 2002-112959 | 4/2002 |
| JP | 2005-177025 | 7/2005 |
| JP | 2006-072098 | 3/2006 |
| JP | 2009-183618 | 8/2009 |
| JP | 2012-139435 | 7/2012 |
| JP | 2012-147882 | 8/2012 |
| JP | 2012-196307 | 10/2012 |
| JP | 5075658 | 11/2012 |
| JP | 2012-196307 | 12/2012 |
| WO | 2014/189091 | 11/2014 |

* cited by examiner

ENDOSCOPE APPARATUS

CROSS-REFERENCE TO RELATED APPLICATIONS

This is a continuation of International Application PCT/JP2014/084164 which is hereby incorporated by reference herein in its entirety.

This application is based on Japanese Patent Application No. 2014-005132, the contents of which are incorporated herein by reference.

TECHNICAL FIELD

The present invention relates to an endoscope apparatus and relates, in particular, to an endoscope apparatus provided, at the distal end thereof, with a plurality of illumination optical systems in an inserted portion.

BACKGROUND ART

In general, structures such as an illumination optical system that radiates illumination light onto an imaging subject, an observation optical system for observing the imaging subject, a channel for guiding a treatment tool or the like, a nozzle or the like for washing the lens surface of the observation optical system, and so on, are disposed at a distal-end portion of an endoscope apparatus. In addition, an endoscope apparatus that efficiently irradiates a viewing field having a wide viewing angle by having a plurality of illumination optical systems disposed therein has been proposed. In this case, because the individual structures need to be efficiently disposed in a limited space, the illumination optical systems are disposed so as to flank the observation optical system.

Also, an endoscope apparatus with which it is possible to perform normal observation and near-field observation by changing the focal distance by moving some of the lenses in the observation optical system has been proposed.

As an example of such an endoscope apparatus, Patent Literature 1 discloses an endoscope apparatus with which, by setting the operating range for achieving the best focusing position within an area in which illumination beams emitted from a plurality of illumination windows overlap, it is possible to illuminate an imaging subject with sufficient brightness and with small illumination unevenness during magnifying near-field observation.

In addition, Patent Literature 2 discloses an endoscope apparatus with which the variability in the observation regions during near-field observation is minimized by providing an illuminating means at a position at which illuminances of peripheral portions become equal to or less than twice the illuminances at center portions of observation regions on either side of the observation optical system.

Furthermore, Patent Literatures 3 to 5 disclose endoscope apparatuses that are provided with, in the distal-end surface of an inserted portion, an observation window of an observation optical system, a forceps port having a circular shape in which the diameter thereof is greater than that of the observation window, and a plurality of light radiation windows through which illumination light is radiated, wherein the plurality of light radiation windows are disposed so as to flank the observation window.

CITATION LIST

Patent Literature

{PTL 1} Japanese Unexamined Patent Application, Publication No. 2001-346752
{PTL 2} Japanese Unexamined Patent Application, Publication No. 2000-37345
{PTL 3} Japanese Unexamined Patent Application, Publication No. 2001-166223
{PTL 4} Japanese Unexamined Patent Application, Publication No. 2005-177025
{PTL 5} Publication of Japanese Patent No. 5075658

SUMMARY OF INVENTION

Solution to Problem

An aspect of the present invention is an endoscope apparatus including an observation optical system that is provided at a distal end of an inserted portion of the endoscope apparatus to observe an observation subject; and a plurality of illumination optical systems that are provided in the inserted portion and that illuminate the same viewing field by distributing illumination light emitted from a light source over the observation subject, wherein, of the plurality of the illumination optical systems, the distance from the observation optical system to the widest-angle illumination optical system is smaller than the distance from the observation optical system to the narrowest-angle illumination optical system.

DESCRIPTION OF EMBODIMENTS

First Embodiment

An endoscope apparatus according to a first embodiment of the present invention will be descried below with reference to the drawings.

Figure 1:
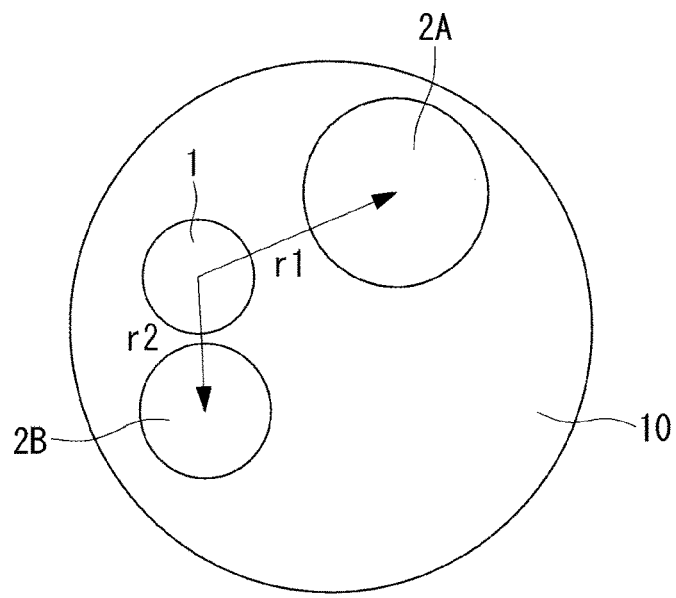
FIG. 1 is an explanatory diagram showing a distal-end surface of an inserted portion of an endoscope apparatus according to a first embodiment of the present invention.

FIG. 1 shows an inserted portion distal-end surface 10 of an endoscope apparatus according to this embodiment. As shown in FIG. 1, the endoscope apparatus is provided with, at an inserted-portion distal end of the endoscope apparatus, an observation optical system 1 for observing an observation subject and two illumination optical systems 2A and 2B that illuminate the same viewing field by distributing illumination light emitted from a light source (not shown) over the observation subject. Note that, in addition to these components, the endoscope apparatus is provided with a gas/liquid feeding nozzle, a forceps port, and so forth; however, descriptions thereof will be omitted in this embodiment. The plurality of illumination optical systems 2A and 2B have different light-distribution characteristics from each other, and the illumination optical system 2B has a light distribution with a wider angle than that of the illumination optical system 2A.

Also, the wide-angle illumination optical system 2B is disposed so that the distance thereto from the observation optical system 1 becomes smaller than the distance from the observation optical system 1 to the narrow-angle illumination optical system 2A. In other words, the narrow-angle illumination optical system 2A is disposed at a position separated from the center of the observation optical system by r1, and the wide-angle illumination optical system 2B is disposed at a position separated therefrom by r2 (r1>r2).

When performing near-field observation, the entire viewing-field region is irradiated with the illumination light mainly by using the wide-angle illumination optical system 2B, and, when performing normal observation, for example, when observing far into the center portion of a lumen, the light is radiated like a spotlight by using the narrow-angle illumination optical system 2A. Because of this, by disposing the illumination optical systems as described above, it is possible to radiate optimal illumination light by using the illumination optical system 2A or 2B depending on the situation with respect to near and far illumination requirements, which differ from each other; and thus, it is possible to ensure, from the distant view to the near view, a satisfactory brightness and light distribution and to perform superior observation in which halation is also decreased.

In this embodiment, by disposing, in the narrow-angle illumination optical system 2A, a light guide having a larger diameter than the size of the radiation window of the illumination optical system 2B in accordance with the size of the radiation window of the illumination optical system 2A, the exiting light level of the illumination optical system 2A is made greater than the light level of the illumination optical system 2B. By doing so, the brightness for the distant view becomes favorable, which facilitates achieving sufficient brightness at a more-distant site, and thus, this illumination arrangement allows sufficient brightness to be obtained from a close-up view to a distant view.

The wide-angle illumination optical system 2B is disposed close to the observation optical system 1, which makes it suitable mainly as illumination for a close-up view. Because the brightness is sufficient during near-field observation, the illumination optical system has a light guide having a small diameter, that is, a low exiting light level. Because the location of the illumination window is easily recognized by using an acquired endoscope image, it is desirable to use an illumination optical system having the best possible light distribution when performing near-field observation; however, by using the illumination optical system 2B, an image in which sufficient brightness reaches from the center to periphery thereof is also obtained during a close-up view.

In addition, because of the wide-angle light distribution, an image tends to have halation at the periphery when observing a lumen; however, because the exiting light level is minimized by decreasing the light-guide diameter, the above-described influence can be considerably decreased.

The narrow-angle illumination optical system 2A is disposed relatively far away from the observation optical system 1, which makes it suitable mainly as illumination when performing observation in a distant view. When performing observation in a distant view, it is necessary to employ an illumination optical system that has a high exiting light level and in which a satisfactory light guide is installed so that a bright view can be achieved at a far site. At this time, from the viewpoint of decreasing halation, it is desirable that the angle of the light distribution be not exceedingly large, and, when observing a lumen such as the esophagus, large intestine, or the like, in particular, it is possible to obtain an image that is sufficiently bright to the periphery of an endoscope screen, even if the angle becomes considerably small.

In addition, it is preferable that the angular characteristics of the narrow-angle illumination optical system 2A and the wide-angle illumination optical system 2B satisfy the conditional expression below:

$$\gamma B(60°)/\gamma A(60°) > 1 \tag{1},$$

where γA(60°) is the exiting-light-level ratio with respect to the center (emitting angle 0°) of the narrowest-angle illumination optical system when the emitting angle is 60°, and γB(60°) is the exiting-light-level ratio with respect to the center (emitting angle 0°) of the widest-angle illumination optical system when the emitting angle is 60°.

The region when the emitting angle is 60° roughly corresponds to the viewing-field region that extends to the peripheral portions of the observation region of the endoscope apparatus. Therefore, the magnitude of the exiting light level when the emitting angle is 60° becomes a determining factor in the light distribution. When the range of conditional expression (1) is exceeded, the angular characteristics of the individual illumination optical systems end up being inverted. In other words, there is a problem in that it is not possible to achieve sufficient brightness for an imaging subject at a far distance, and that the center portion becomes darker as compared with the peripheral portions when an imaging subject is at a close distance.

Because of this, by satisfying the above-described conditional expression (1), uniform illumination is achieved with the illumination light both when performing a normal observation and when performing a near-field observation, and thus, it is possible to ensure satisfactory light distribution and brightness.

It is more desirable that the endoscope apparatus satisfy the following conditional expression (1') or (1") instead of conditional expression (1):

$$\gamma B(60°)/\gamma A(60°) \geq 1.2 \quad (1'),)$$

$$\gamma B(60°)/\gamma A(60°) > 1.6 \quad (1'').$$

In addition, it is preferable that the angular characteristics of the narrow-angle illumination optical system 2A and the wide-angle illumination optical system 2B satisfy the conditional expressions below:

$$0.01 < \gamma A(50°) < 0.25 \quad (2) \text{ and}$$

$$0.10 < \gamma B(50°) < 0.40 \quad (3),$$

where γA(50°) is the exiting-light-level ratio with respect to the center (emitting angle 0°) of the narrowest-angle illumination optical system when the emitting angle is 50°, and γB(50°) is the exiting-light-level ratio with respect to the center (emitting angle 0°) of the widest-angle illumination optical system when the emitting angle is 50°.

The angular characteristics of the individual illumination optical systems are often such that the exiting-light-level ratio of the narrow-angle illumination optical system 2A is greater than or about equal to that of the wide-angle illumination optical system 2B up to the emitting angle of about 0 to 30° near the center of the optical axis. However, at the emitting angle of about 50 to 60° near the center of the optical axis, the exiting-light-level ratio of the wide-angle illumination optical system 2B is greater than that of the narrow-angle illumination optical system 2A, and, at the emitting angle of 60°, the exiting-light-level ratio of the wide-angle illumination optical system 2B is always greater.

Conditional expressions (2) and (3) are exiting-light-level ratios of the individual illumination optical systems when the emitting angle is 50°.

It is preferable that the angular characteristics of the wide-angle illumination optical system satisfy conditional expression (2) for the following reasons. When the lower limit of conditional expression (2) is not reached a wide-angle light distribution cannot be achieved, and, when the upper limit of conditional expression is exceeded, although a wide-angle light distribution is achieved, it is undesirable because the center becomes dark, thus also affecting the center brightness in a distant view.

In addition, it is preferable that the angular characteristics of the narrow-angle illumination optical system satisfy conditional expression (3) for the following reasons. When the lower limit of conditional expression (3) is not reached, the angle of the light distribution becomes too narrow, which is undesirable because the brightness at the peripheral portion of the screen is also affected. In addition, when the upper limit of conditional expression (3) is exceeded, although the light distribution is improved, a decrease in the center brightness becomes problematic.

Furthermore, it is desirable that, when the emitting angle of view is 50°, the exiting-light-level ratios of the narrow-angle illumination optical system 2A and the wide-angle illumination optical system 2B satisfy conditional expression below:

$$\gamma B(50°)/\gamma A(50°) > 1.0 \quad (4).$$

As with conditional expression (1), conditional expression (4) is a conditional expression that determines the magnitude of the light distributions of the wide-angle illumination optical system 2B and the narrow-angle illumination optical system 2A. The following problems arise in the case in which the endoscope apparatus does not satisfy conditional expression (4). Specifically, in the endoscope apparatus, the difference between the light distributions of the wide-angle illumination optical system 2B and the narrow-angle illumination optical system 2A is decreased, making it difficult to recognize the difference therebetween. In addition, in particular, the center becomes dark when performing near-field observation or the like, and it becomes impossible to ensure a satisfactory light distribution and brightness.

Note that it is more preferable that the endoscope apparatus satisfy the following conditional expression (4') instead of conditional expression (4):

$$\gamma A(50°)/\gamma B(50°) > 1.2 \quad (4').$$

In this embodiment, the endoscope apparatus has the wide-angle illumination optical system 2B disposed relatively close to the observation optical system and the narrow-angle illumination optical system 2A disposed relatively far away therefrom. With regard to the positional relationship in which the illumination optical system 2B is disposed relatively close to the observation optical system and the illumination optical system 2A is disposed relatively far away therefrom, specifically, it is preferable that the following conditional expression be satisfied:

$$1.0 < r1/r2 < 3.0 \quad (5),$$

where r1 is the distance between the center of the observation optical system and the center of the narrow-angle illumination optical system, and r2 is the distance between the center of the observation optical system and the center of the wide-angle illumination optical system.

Because the narrow-angle illumination optical system 2A is disposed too far away from the observation optical system 1 when the upper limit of conditional expression (5) is exceeded, the diameter of the distal-end portion of the endoscope apparatus is consequently increased, which is undesirable. On the other hand, when the lower limit of conditional expression is not reached, the wide-angle illumination optical system 2B is positioned away from the observation optical system 1, and, because the wide-angle illumination optical system 2B is positioned closer to the end portion of the distal-end portion of the endoscope apparatus, the influence of halation exceeds a negligible level.

It is more preferable that the endoscope apparatus satisfy conditional expression (5') instead of conditional expression (5):

$$1.02 < r1/r2 < 2.55 \quad (5').$$

By increasing the lower limit value of conditional expression (5), it is possible not only to suppress halation but also to achieve a superior light distribution when performing near-field observation. In the range that does not exceed the upper limit of conditional expression (5), it is possible to further decrease the diameter of the endoscope distal-end portion.

In addition, it is preferable that the illumination optical systems installed in the endoscope apparatus satisfy the conditional expressions below:

$$4 < r1/|fw| < 12 \quad (6),$$

$$1 < r2/|fs| < 8 \quad (7), \text{ and}$$

$$0.8 < |fs/fw| < 2.8 \quad (8),$$

where fs is the overall focal distance of the narrow-angle illumination optical system, and fw is the overall focal distance of the wide-angle illumination optical system.

Conditional expression (6) is a conditional expression for halation reduction. Because the light distribution of the illumination optical system having a large light-guide diameter becomes wide when the lower limit of conditional expression (6) is not reached, halation tends to occur in peripheral portions of the screen. In addition, because the angle of the light distribution becomes exceedingly wide and considerably high brightness is also reached outside the viewing-field region of the endoscope image, the illumination efficiency is significantly decreased. Because the illumination optical system is positioned at the end portion of the inserted-portion distal end of the endoscope when the upper limit of conditional expression (6) is exceeded, halation tends to occur.

Because the wide-angle illumination optical system 2B and the observation optical system 1 are close to each other when the lower limit of conditional expression (7) is not reached, the illumination light tends to directly enter the observation optical system 1, which increases the risk of illumination being recognized as flare in the acquired image. In addition, when the upper limit of conditional expression (7) is exceeded, with regard to the arrangement of the components, the illumination optical systems are positioned at the inserted-portion distal end of the endoscope, and halation tends to occur even with the narrow-angle illumination optical system 2A due to a large number of light guides.

Because the focal distance of the narrow-angle illumination optical system 2A is decreased and the light distribution becomes wider when the lower limit of conditional expression (8) is not reached, it is not possible to achieve sufficient center brightness when performing observation at a distant view. In addition, because the focal distance of the wide-angle illumination optical system 2B is decreased when the upper limit of conditional expression (8) is exceeded, the light distribution of the illumination when performing near-field observation deteriorates, which is undesirable because the influences thereof are manifested in the form of illumination unevenness or the like.

It is more preferable that the endoscope apparatus satisfy conditional expressions (6') to (8') instead of the above-described conditional expressions (6) to (8):

$$6 < r1/|fw| < 10 \quad (6'),$$

$$2 < r2/|fs| < 6 \quad (7'), \text{ and}$$

$$1.2 < |fs/fw| < 2.2 \quad (8').$$

In conditional expression (6'), by setting the lower-limit value thereof to be greater than the lower-limit value of conditional expression (6), it is possible to increase the distance from the observation optical system 1, and the light distribution when performing near-field observation is further enhanced. In addition, similarly, by setting the upper-limit value of conditional expression (6') to be lower than the upper-limit value of conditional expression (6), the illumination optical systems are not disposed at peripheral edge portions of the distal-end portion of the inserted portion, and thus, this is effective for further reducing halation.

In addition, by setting the range of conditional expression (7') to be smaller than the range of conditional expression (7), an even greater halation-reduction effect is achieved.

By increasing the lower limit of conditional expression (8'), it is possible to keep even better center brightness when performing observation in a distant view, and, in addition, by decreasing the upper limit, it is possible to further decrease the light-distribution unevenness when performing near-field observation.

Figure 2:
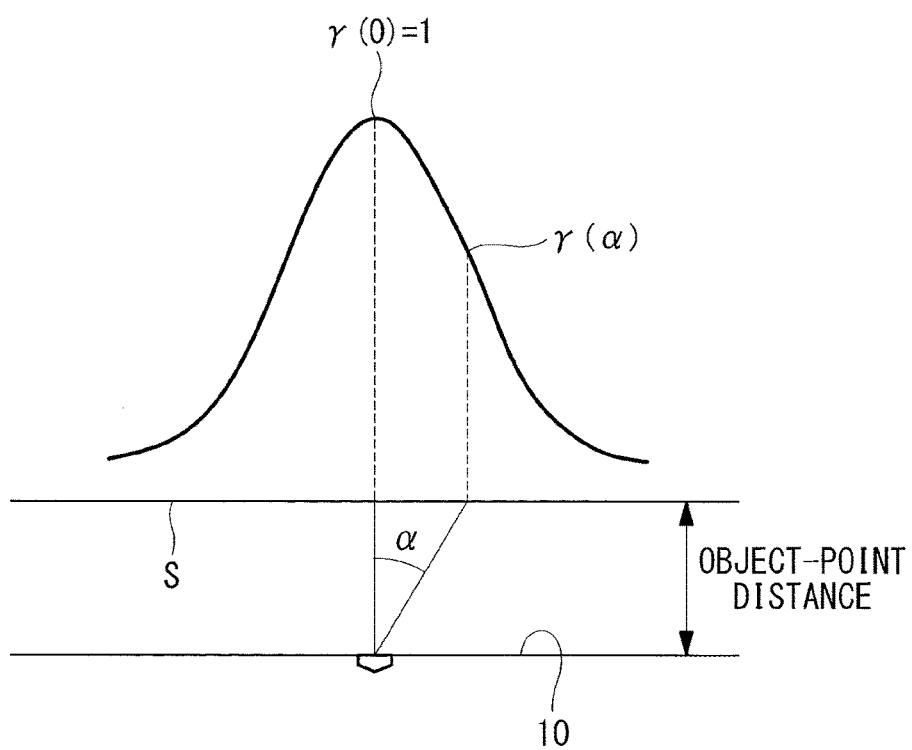
FIG. 2 is a graph showing light-distribution characteristics exhibited by an illumination optical system of the endoscope apparatus according to the first embodiment of the present invention.

FIG. 2 shows the light-distribution characteristics of the illumination optical systems. The curve in FIG. 2 shows a light distribution with respect to an imaging subject S that is separated from the illumination optical systems 2 by a certain distance (equal to or greater than 50 mm, which can be considered to be a sufficient separation). At this time, assuming that the top direction in FIG. 2 is 0°, that the brightness at the 0°-position is $\gamma(0)=1$, and that an angle $\alpha$ is taken in the clockwise direction, the brightness at the angle $\alpha$ is defined as $\gamma(\alpha)$. Note that, because the light distribution is symmetrical, the angle $\alpha$ may be taken counterclockwise from the center.

Figure 3:
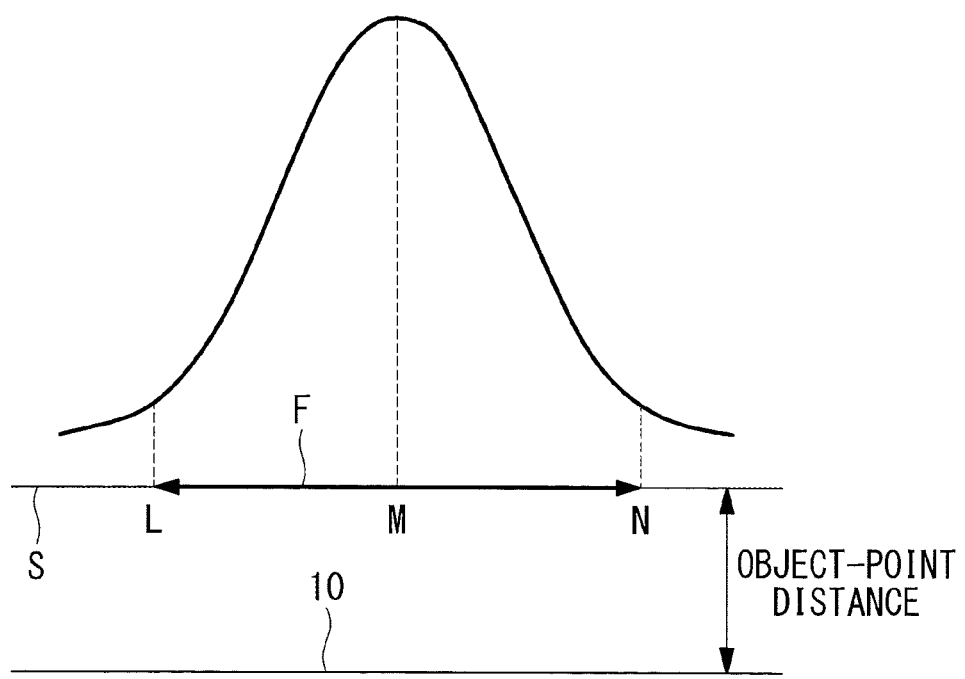
FIG. 3 is a graph showing light-distribution characteristics exhibited by the illumination optical system of the endoscope apparatus according to the first embodiment of the present invention during normal observation.

FIG. 3 shows the light-distribution characteristics of the illumination optical systems when performing normal observation. The curve in FIG. 3 shows a light distribution due to the illumination optical systems, assuming that the imaging subject S is positioned at an object-point distance (equal to or greater than 50 mm) sufficiently separated from the inserted-portion distal-end surface 10 of the endoscope apparatus, that the center of a viewing-field region F of the observation optical system is M, and that values of maximum angles of view are L and N, respectively. The feature of when performing normal observation is that, at a long distance, that is, a distance of 50 mm or greater, the light distribution is not affected by the arrangement of the illumination optical systems, and the shape of the distribution becomes nearly uniform with reference to the center.

Figure 4:
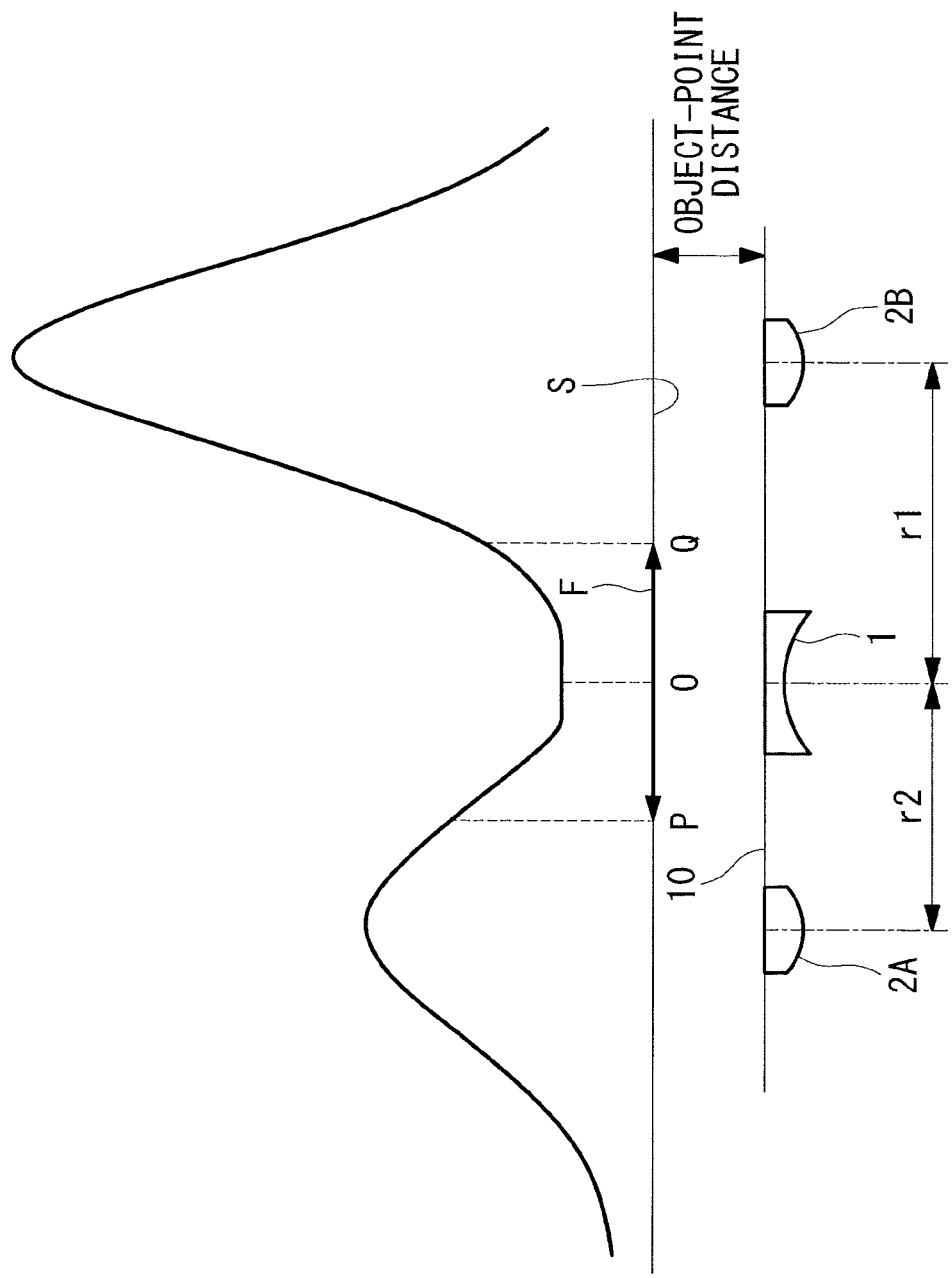
FIG. 4 is a graph showing light-distribution characteristics exhibited by the illumination optical system of the endoscope apparatus according to the first embodiment of the present invention during near-field observation.

FIG. 4 shows the light-distribution characteristics of the illumination optical systems when performing near-field observation. In other words, the curve in FIG. 4 shows a light distribution due to the narrow-angle illumination optical system 2A and the wide-angle illumination optical system 2B. However, it is assumed that the imaging subject S is at a position that is separated from the inserted-portion distal-end surface 10 of the endoscope apparatus, which passes through the centers of the observation optical system 1, the narrow-angle illumination optical system 2A, and the wide-angle illumination optical system 2B, by the object-point distance when performing near-field observation, that the center of the viewing-field region F of the observation optical system 1 is O, and that the most peripheral portions are P and Q, respectively.

The feature when performing near-field observation is that, because the object-point distance in the case of a magnifying endoscope is extremely small, namely, 1.5 mm to 3 mm, the peripheral portion of the viewing-field region sometimes exhibits higher light-distribution characteristics than the center portion thereof, as in the light distribution in FIG. 4.

In the present invention, the illumination optical system having a narrow light distribution is disposed closer to the peripheral portion, and the illumination optical system having a wide light distribution is disposed closer to the center portion so as to achieve superior overall light-distribution characteristics and so as to make the center portion and the peripheral portion as flat as possible.

Figure 5:
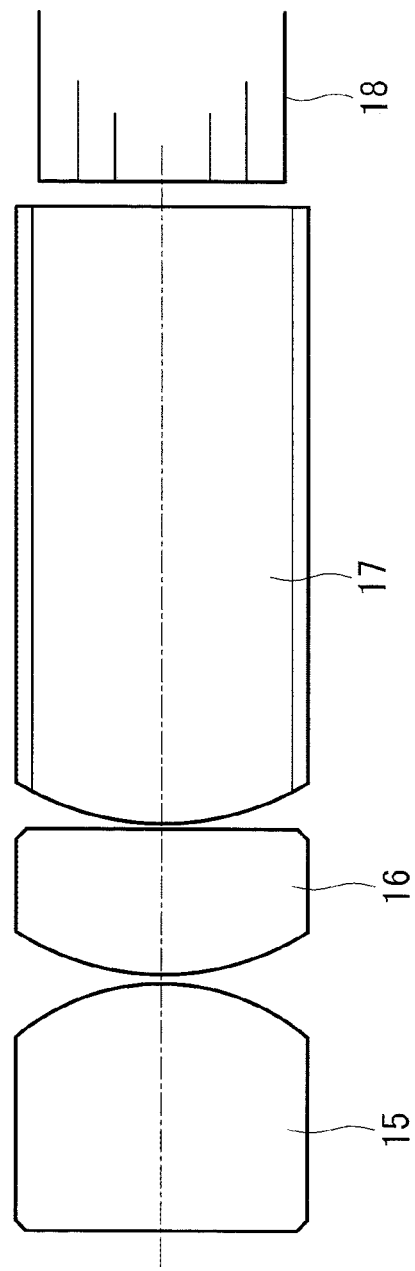
FIG. 5 is a sectional view showing an example configuration of a wide-angle illumination optical system in the endoscope apparatus according to the first embodiment of the present invention.

FIG. 5 is a sectional view showing an example configuration of the wide-angle illumination optical system 2B in this embodiment.

As shown in FIG. 5, the wide-angle illumination optical system 2B is provided with a light guide 18 that guides emitted light from a light source (not shown), a convex lens 15, a convex lens 16, and a glass-rod convex lens 17.

As the illumination optical system, various configurations can be employed, such as a simple configuration with one convex lens, a configuration with one concave lens, a configuration with two convex lenses, or the like. Because the light distribution becomes narrow when the number of lenses is low, the wide-angle illumination optical system 2B in this embodiment has a configuration provided with three convex lenses, as described above.

Figure 6:
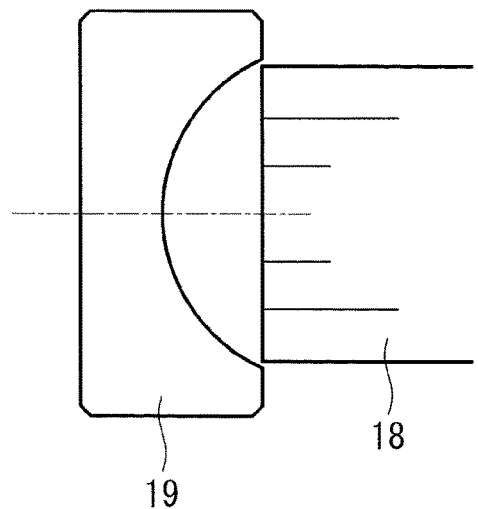
FIG. 6 is a sectional view showing an example configuration of a narrow-angle illumination optical system of the endoscope apparatus according to the first embodiment of the present invention.

FIG. 6 is a sectional view showing an example configuration of the narrow-angle illumination optical system 2A in this embodiment. As shown in FIG. 6, the narrow-angle illumination optical system 2A is provided with a light guide 18 that guides the emitted light from the light source (not shown), and a concave lens 19. By doing so, it is possible to reduce the manufacturing cost by employing a simple configuration.

Note that it is also possible to employ a configuration provided with three convex lenses, as with the wide-angle illumination optical system 2B.

Note that, when the light level at angle of 0° at the center is assumed to be 1, light-distribution characteristics with respect to angles of 30°, 50°, and 60° for the light guides, which guide the illumination light to the illumination optical systems from the light source, are as follows:
$\gamma(0°)=1.00$,
$\gamma(30°)=0.25$,
$\gamma(50°)=0.005$, and
$\gamma(60°)=0.001$.

Note that the light-distribution characteristics of the individual illumination optical systems are assumed to be values obtained on the basis of the illumination characteristics of the light guides described above, and are normalized by assuming that the exiting light level at the center when the emitting angle is 0° is 1.

In addition, with regard to the exiting light levels of the individual illumination optical systems, it is desirable that conditional expression (9), described below, be satisfied:

$$0.3 < (\varphi B \cdot fw)/(\varphi A \cdot fs) < 1.2 \tag{9}$$

where $\varphi A$ is the light-guide diameter of the narrow-angle illumination optical system, and $\varphi B$ is the light-guide diameter of the wide-angle illumination optical system.

When the lower limit of conditional expression (9) is not reached, the exiting light level of the wide-angle illumination optical system 2B becomes relatively low, which increases the influence of the narrow-angle illumination optical system 2A; however, when performing near-field observation, in the case of magnifying observation in particular, it becomes difficult to achieve a better light distribution. This makes it easier to recognize brightness intensity differences on the screen, thus creating an image in which the position of the narrow-angle illumination optical system can be identified.

On the other hand, when the upper limit of conditional expression (9) is exceeded, the exiting light level of the narrow-angle illumination optical system 2A becomes relatively low, which makes the brightness at the center insufficient when performing observation in a distant view, and thus, there is a concern that screening is adversely affected. Note that the exiting light level can be considered to be proportional to the light-guide diameter, and, furthermore, the light-guide diameter can be considered in terms of the number of the light guides.

Furthermore, with regard to the exiting light level, it is preferable that conditional expression (10), described below, be satisfied. Specifically, it is preferable that the light-guide diameter of the narrow-angle illumination optical system 2A be greater than the light-guide diameter of the wide-angle illumination optical system 2B by a factor 0.8 or more.

$$\varphi A/\varphi V > 0.8 \tag{10}$$

In the case in which conditional expression (10) is not satisfied, it is not possible to ensure a satisfactory light distribution in a distant view, and thus, it is not possible to achieve satisfactory brightness in the imaging subject.

In the case in which it is necessary to ensure sufficient brightness in a view at a greater distance and to obtain a clear image deeper into a lumen, in particular, in the esophagus, large intestine, or the like, it is possible to ensure a sufficient brightness in a distant view by applying conditional expression (10') instead of conditional expression (10).

$$\varphi A/\varphi V > 1.1 \tag{10'}$$

Furthermore, by satisfying conditional expression (10") instead of conditional expression (10'), it is possible to ensure sufficient brightness in a view at a greater distance.

$$\varphi A/\varphi V > 1.3 \tag{10"}$$

In addition, in this embodiment, in order to enhance observability when performing observation in a near view in particular, it is preferable that the observation optical system 1 satisfy conditional expression (11) below:

$$0.08 < ft/L < 1.2 \tag{11},$$

where L is the closest observation distance, and ft is the focal distance of the observation optical system when performing near-point observation.

Because the closest observation distance is decreased even more when the lower limit of conditional expression (11) is not reached, illumination unevenness occurs even if the light distributions of the illumination optical systems are enhanced. In addition, when the upper limit of conditional expression (11) is exceeded, illumination unevenness does not occur even if the light distributions of the illumination optical systems are poor when performing close-range observation, and the illumination optical systems do not need to be devised as described above.

By satisfying conditional expression (11') instead of conditional expression (11), it is possible to further improve the light distribution.

$$0.12 < ft/L < 0.86 \tag{11'}$$

As has been described above, with this embodiment, both when performing normal observation and when performing near-field observation, uniform illumination is achieved from near sites to far sites and satisfactory light distribution and brightness are ensured while ensuring sufficiently low invasiveness, and thus, it is possible to perform a superior observation in which halation is less likely to occur.

Second Embodiment

Figure 7:
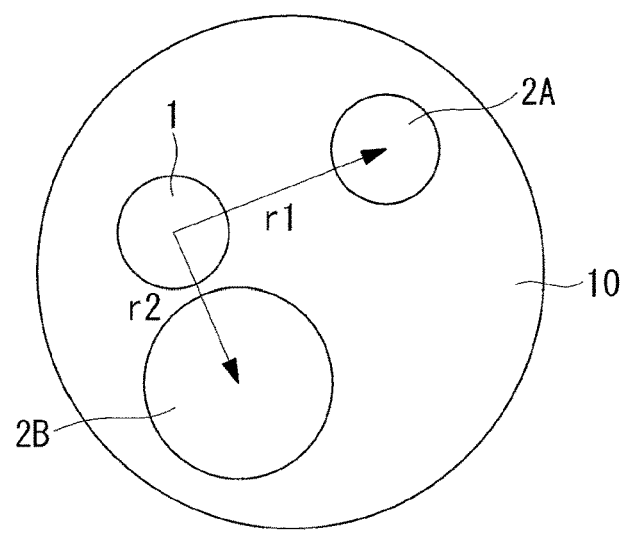
FIG. 7 is an explanatory diagram showing a distal-end surface of an inserted portion of an endoscope apparatus according to a second embodiment of the present invention.

FIG. 7 shows the configuration of an inserted-portion distal end in an endoscope apparatus according to a second embodiment of the present invention. As shown in FIG. 7, the endoscope apparatus according to this embodiment is provided with, at the inserted-portion distal end of the endoscope apparatus, the observation optical system 1 for observing the observation subject and the two illumination optical systems 2A and 2B that illuminate the same viewing field by distributing illumination light emitted from the light source (not shown) over the observation subject. Note that, in addition to these components, the endoscope apparatus is provided with a gas/liquid feeding nozzle, a forceps port, and so forth; however, descriptions thereof will be omitted in this embodiment. The plurality of illumination optical systems 2A and 2B have different light-distribution characteristics from each other, and the illumination optical system 2B has a light distribution with a wider angle than that of the illumination optical system 2A.

As shown in FIG. 7, the wide-angle illumination optical system 2B is disposed so that the distance thereto from the observation optical system 1 becomes smaller than the distance from the observation optical system 1 to the narrow-angle illumination optical system 2A. In other words, the narrow-angle illumination optical system 2A is disposed at a position separated from the center of the observation optical system by r1, and the wide-angle illumination optical system 2B is disposed at a position separated therefrom by r2 (r1>r2). By disposing the observation optical system 1 and the illumination optical system 2B so that the distance thereto from the observation optical system 1 is smaller than the distance to the illumination optical system 2A, it is possible to ensure, from the distant view to the near view, a satisfactory brightness and light distribution and to perform superior observation in which halation is also decreased.

In this embodiment, the illumination optical systems 2A and 2B are disposed as described above, and, furthermore, the light guide having a small diameter is employed in the narrow-angle illumination optical system 2A, thus making the exiting light level of the narrow-angle illumination optical system 2A a lower light level than the exiting light level of the wide-angle illumination optical system 2B. By doing so, at all object-point distances from a close-up view to a distant view, uniform, superior brightness is achieved from the center portion of a display region to the most peripheral portion of the screen in an acquired observation image, which makes halation even less likely to occur. The arrangement in which the illumination optical system 2B is disposed so that the distance thereto from the observation optical system 1 is smaller than the distance to the illumination optical system 2A is particularly suitable for a near-field-observation subject, and is advantageous for an endoscope apparatus having a magnifying observation function.

The wide-angle illumination optical system 2B is disposed close to the observation optical system 1, which makes it suitable as illumination mainly for close-up viewing. By using the wide-angle illumination optical system 2B, an image in which sufficient brightness reaches from the center to the periphery thereof is obtained at any object-point distance.

The narrow-angle illumination optical system 2A is disposed relatively far away from the observation optical system 1, which makes it suitable as illumination mainly when performing observation in a distant view. In addition, the light guide employed in the narrow-angle illumination optical system 2A has a smaller diameter than the light guide employed in the illumination optical system 2B. Thus, the narrow-angle illumination optical system 2A ensures sufficient brightness when performing observation in a distant view in combination with the illumination system having a wide-angle light distribution, in which the light-guide diameter is large.

Note that the individual illumination optical systems 2A and 2B in this embodiment also satisfy the above-described conditional expressions (1) to (4). In addition, it is more preferable that the above-described conditional expressions (5) to (10) be satisfied.

In the first and second embodiments, described above, although examples in which the endoscope apparatus is provided with the two illumination optical systems 2A and 2B have been described, it is also possible to employ a configuration provided with three or more illumination optical systems. FIGS. 8 to 11 show examples in which three illumination optical systems are disposed.

Figure 8:
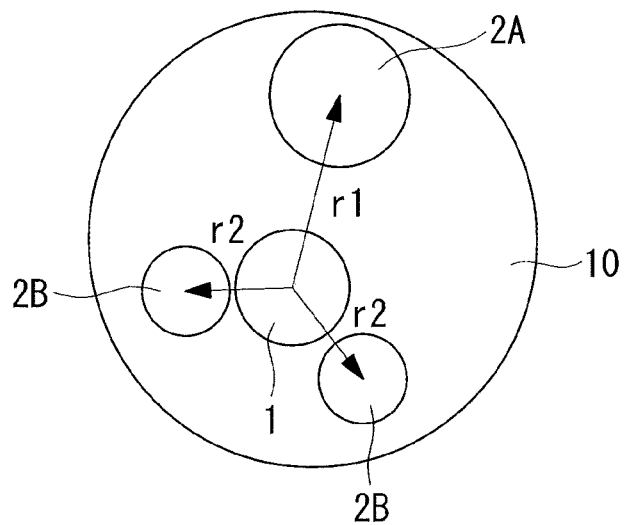
FIG. 8 is an explanatory diagram showing a distal-end surface of an inserted portion of an endoscope apparatus according to another example of the present invention.

In the arrangement in FIG. 8, one narrow-angle illumination optical system 2A is at a position that is relatively far away from the observation optical system 1, and two wide-angle illumination optical systems 2B are disposed at positions that are relatively close to the observation optical system 1. The arrangement as shown in FIG. 8 is suitable in the case in which it is necessary to eliminate illumination unevenness by achieving a superior light distribution when performing near-field observation.

Figure 9:
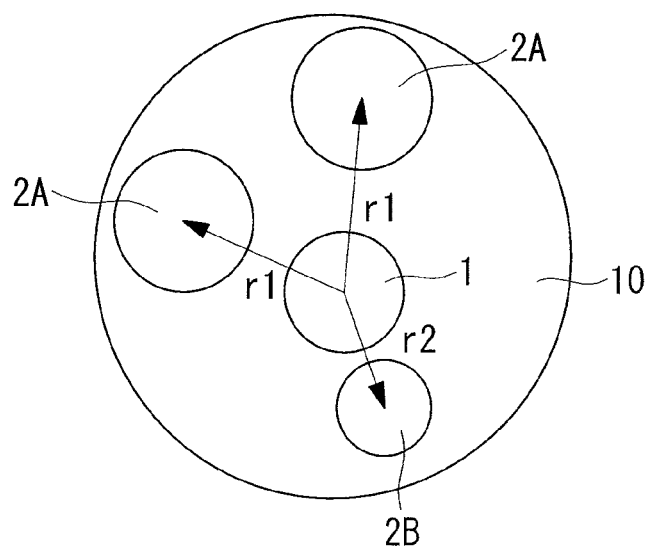
FIG. 9 is an explanatory diagram showing a distal-end surface of an inserted portion of an endoscope apparatus according to another example of the present invention.

In the example shown in FIG. 9, two narrow-angle illumination optical systems 2A in which the light-guide diameter is large and one wide-angle illumination optical system 2B in which the light-guide diameter is small are provided. This configuration is suitable in the case in which the center brightness when performing observation in a distant view is important.

Figure 10:
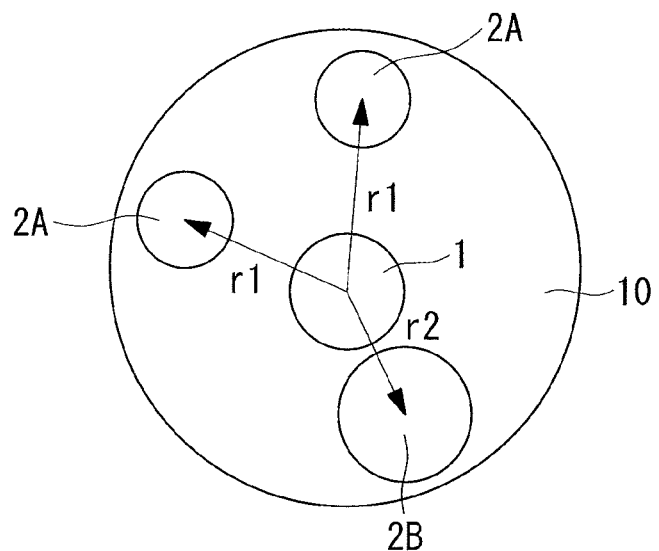
FIG. 10 is an explanatory diagram showing a distal-end surface of an inserted portion of an endoscope apparatus according to another example of the present invention.

In the example shown in FIG. 10, two narrow-angle illumination optical systems 2A in which the light-guide diameters are small and one wide-angle illumination optical system 2B in which the light-guide diameter is large are provided. This configuration is suitable for the case in which both the center brightness in a distant view and the light distribution from a near view to a distant view are important.

Figure 11:
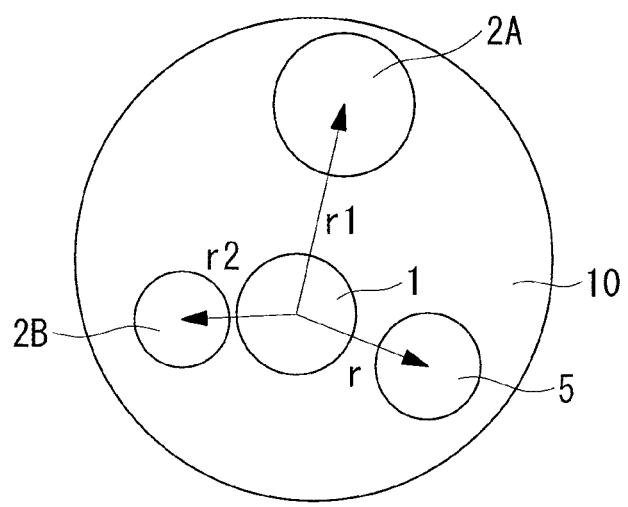
FIG. 11 is an explanatory diagram showing a distal-end surface of an inserted portion of an endoscope apparatus according to another example of the present invention.

In the example shown in FIG. 11, an intermediate illumination optical system 5 between a wide-angle light distribution and narrow-angle light distribution is provided. In this configuration, the brightness when performing observation in a distant view, illumination unevenness when performing near-field observation, and halation are individually taken into consideration, and an overall balance is important.

EXAMPLES

Next, Examples 1 to 7 of the observation optical system according to one of the above-described embodiments will be described. In the individual Examples, r1 is the distance from the center of the observation optical system to the center of the narrow-angle illumination optical system, r2 is the distance from the center of the observation optical system to the center of the wide-angle illumination optical system, γA(50°) is the angular characteristics of the illuminance of the narrow-angle illumination optical system, γB(50°) is the angular characteristics of the illuminance of the wide-angle illumination optical system, fs is the overall focal distance of the narrow-angle illumination optical system, fw is the overall focal distance of the wide-angle illumination optical system, φA is the light-guide diameter of the narrow-angle illumination optical system, and φB is the light-guide diameter of the wide-angle illumination optical system. In addition, in lens data included in the individual Examples, r is the radius of curvature (unit: mm), d is the surface spacing (mm), and Ne is the refractive index with respect to the e-line.

Example 1

An endoscope apparatus according to Example 1 of the present invention is provided with one narrow-angle illumination optical system and one wide-angle illumination optical system. The narrow-angle illumination optical system and the wide-angle illumination optical system in this Example both are provided with three convex lenses, as shown in FIG. 5. Of the three convex lenses, the clad of the glass-rod convex lens is a glass having a refractive index of 1.518.

Lens data for the illumination optical systems according to Example 1 are shown below.

(Narrow-Angle Illumination Optical System)
Lens Data

| Surface Number | r | d | Nd |
|---|---|---|---|
| 1 | ∞ | 1.60 | 1.888 |
| 2 | −1.20 | 0.05 | |
| 3 | 3.12 | 0.72 | 1.888 |
| 4 | −3.12 | 0.06 | |
| 5 | 2.28 | 3.48 | 1.812 |
| 6 | ∞ | | |

Miscellaneous Data
Focal Distance fs: 0.74 mm
r1: 3.8 mm
Light-Distribution Characteristics
γA(60°): 0.02
γA(50°): 0.13
γA(30°): 0.61
γA(0°): 1.0
Light-Guide Diameter φA: 1.32 mm (Wide-Angle Illumination Optical System)
Lens Data

| Surface Number | r | d | Nd |
|---|---|---|---|
| 1 | ∞ | 1.00 | 1.888 |
| 2 | −1.60 | 0.03 | |
| 3 | 1.60 | 0.60 | 1.888 |
| 4 | −1.60 | 0.04 | |
| 5 | 1.50 | 2.50 | 1.734 |
| 6 | ∞ | | |

Miscellaneous Data
Focal Distance fw: 0.58 mm
r2: 3.6 mm
Light-Distribution Characteristics
γB(60°): 0.06
γB(50°): 0.18
γB(30°): 0.58
γB(0°): 1.0
Light-Guide Diameter φB: 1.1 mm Example 2

An endoscope apparatus according to Example 2 of the present invention is provided with one narrow-angle illumination optical system and one wide-angle illumination optical system. The narrow-angle illumination optical system in this embodiment is formed of a concave lens and a light guide, as shown in FIG. 6. In addition, the wide-angle illumination optical system is provided with three convex lenses, as shown in FIG. 5. Of the three convex lenses, the clad of the glass-rod convex lens is a glass having a refractive index of 1.518.

Lens data for the illumination optical systems according to Example 2 are shown below.

(Narrow-Angle Illumination Optical System)
Lens Data

| Surface Number | r | d | Nd |
|---|---|---|---|
| 1 | ∞ | 0.4 | 1.888 |
| 2 | 0.84 | 0. | |

Miscellaneous Data
Focal Distance fs: −0.945 mm
r1: 4.8 mm
Light-Distribution Characteristics
γA(60°): 0.03
γA(50°): 0.10
γA(30°): 0.52
γA(0°): 1.0
Light-Guide Diameter φA: 1.5 mm (Wide-Angle Illumination Optical System)
Lens Data

| Surface Number | r | d | Nd |
|---|---|---|---|
| 1 | ∞ | 1.10 | 1.888 |
| 2 | −1.000 | 0.04 | |
| 3 | 1.200 | 0.65 | 1.888 |
| 4 | ∞ | 0.02 | |
| 5 | 1.250 | 2.75 | 1.812 |
| 6 | ∞ | | |

Miscellaneous Data
Focal Distance fw: 0.54 mm
r2: 2.2 mm
Light-Distribution Characteristics
γB(60°): 0.05
γB(50°): 0.17
γB(30°): 0.63
γB(0°): 1.0
Light-Guide Diameter φB: 1.1 mm Example 3

An endoscope apparatus according to Example 3 of the present invention is provided with one narrow-angle illumination optical system and one wide-angle illumination optical system. The narrow-angle illumination optical system and the wide-angle illumination optical system in this embodiment are both provided with three convex lenses, as shown in FIG. 5. Of the three convex lenses, the clad of the glass-rod convex lens is a glass having a refractive index of 1.518.

Lens data for the illumination optical systems according to Example 3 are shown below.

(Narrow-angle Illumination Optical System)
Lens Data

| Surface Number | r | d | Nd |
|---|---|---|---|
| 1 | ∞ | 1.80 | 1.888 |
| 2 | −2.800 | 0.06 | |
| 3 | 3.960 | 0.75 | 1.888 |
| 4 | −2.000 | 0.06 | |
| 5 | 4.000 | 3.60 | 1.734 |
| 6 | ∞ | | |

Miscellaneous Data
Focal Distance fs: 0.99 mm
r1: 4.1 mm
Light-Distribution Characteristics
γA(60°): 0.05
γA(50°): 0.14
γA(30°): 0.56
γA(0°): 1.0
Light-Guide Diameter φA: 1.8 mm (Wide-Angle Illumination Optical System)
Lens Data

| Surface Number | r | d | Nd |
|---|---|---|---|
| 1 | ∞ | 1.30 | 1.888 |
| 2 | −2.000 | 0.05 | |
| 3 | 2.000 | 0.75 | 1.888 |
| 4 | −2.000 | 0.05 | |
| 5 | 2.000 | 3.00 | 1.734 |
| 6 | ∞ | | |

Miscellaneous Data
Focal Distance fw: 0.73 mm
r2: 3.2 mm
Light-Distribution Characteristics
γB(60°): 0.06
γB(50°): 0.17
γB(30°): 0.57
γB(0°): 1.0 Light-Guide Diameter φB: 1.38 mm Example 4

An endoscope apparatus according to Example 4 of the present invention is provided with one narrow-angle illumination optical system and one wide-angle illumination optical system. The narrow-angle illumination optical system in this embodiment is formed of a concave lens and a light guide, as shown in FIG. 6. In addition, the wide-angle illumination optical system is provided with three convex lenses, as shown in FIG. 5. Of the three convex lenses, the clad of the glass-rod convex lens is a glass having a refractive index of 1.518.

Lens data for the illumination optical systems according to Example 4 are shown below.

(Narrow-Angle Illumination Optical System)
Lens Data

| Surface Number | r | d | Nd |
|---|---|---|---|
| 1 | ∞ | 0.3 | 1.888 |
| 2 | 0.616 | 0. | |

Miscellaneous Data
Focal Distance fs: −0.694 mm
r1: 2.8 mm
Light-Distribution Characteristics
γA(60°): 0.03
γA(50°): 0.10
γA(30°): 0.52
γA(0°): 1.0
Light-Guide Diameter φA: 1.1 mm (Wide-Angle Illumination Optical System)
Lens Data

| Surface Number | r | d | Nd |
|---|---|---|---|
| 1 | ∞ | 1.20 | 1.888 |
| 2 | −1.090 | 0.03 | |
| 3 | 1.310 | 0.70 | 1.888 |
| 4 | ∞ | 0.03 | |
| 5 | 1.365 | 3.00 | 1.812 |
| 6 | ∞ | | |

Miscellaneous Data
Focal Distance fw: 0.587 mm
r2: 2.4 mm
Light-Distribution Characteristics
γB(60°): 0.05
γB(50°): 0.17
γB(30°): 0.63
γB(0°): 1.0
Light-Guide Diameter φB: 1.2 mm Example 5

An endoscope apparatus according to Example 5 of the present invention is provided with one narrow-angle illumination optical system and one wide-angle illumination optical system. The narrow-angle illumination optical system and the wide-angle illumination optical system in this embodiment are both provided with three convex lenses, as shown in FIG. 5. Of the three convex lenses, the clad of the glass-rod convex lens is a glass having a refractive index of 1.518.

Lens data for the illumination optical systems according to Example 5 are shown below.

(Narrow-Angle Illumination Optical System)
Lens Data

| Surface Number | r | d | Nd |
|---|---|---|---|
| 1 | ∞ | 1.60 | 1.888 |
| 2 | −1.20 | 0.05 | |
| 3 | 3.12 | 0.72 | 1.888 |
| 4 | −3.12 | 0.06 | |
| 5 | 2.28 | 3.48 | 1.812 |
| 6 | ∞ | | |

Miscellaneous Data
Focal Distance fs: 0.74 mm
r1: 4.0 mm
Light-Distribution Characteristics
γA(60°): 0.02
γA(50°): 0.13
γA(30°): 0.61
A(0°): 1.0
Light-Guide Diameter φA: 1.32 mm (Wide-Angle Illumination Optical System)
Lens Data

| Surface Number | r | d | Nd |
|---|---|---|---|
| 1 | ∞ | 1.30 | 1.888 |
| 2 | −2.000 | 0.05 | |
| 3 | 2.000 | 0.75 | 1.888 |
| 4 | −2.000 | 0.05 | |
| 5 | 2.000 | 3.00 | 1.734 |
| 6 | ∞ | | |

Miscellaneous Data
Focal Distance fw: 0.73 mm
r2: 3.0 mm
Light-Distribution Characteristics
γB(60°): 0.06
γB(50°): 0.17
γB(30°): 0.57
γB(0°): 1.0
Light-Guide Diameter φB: 1.38 mm

Example 6

Figure 12:
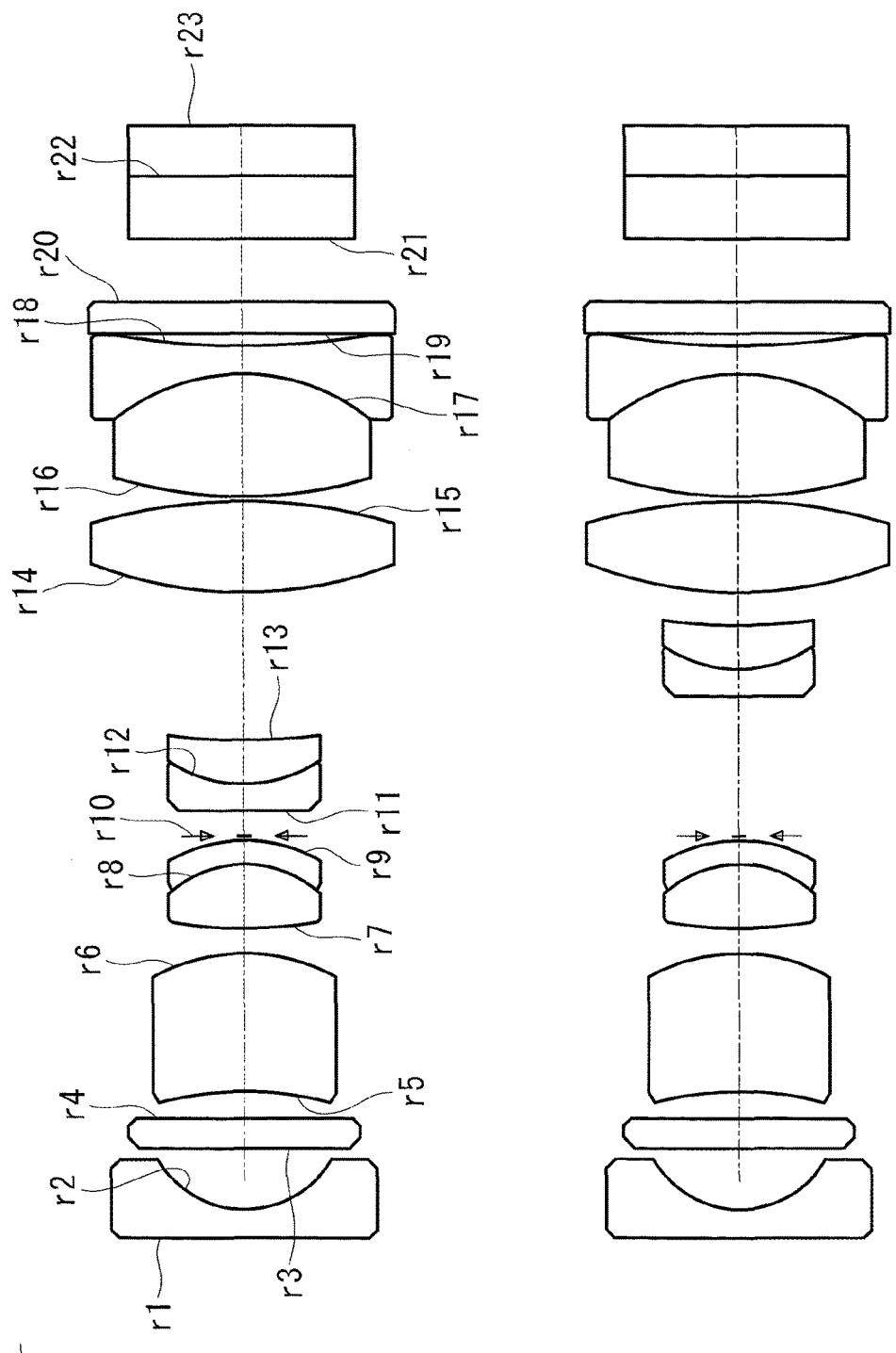
FIG. 12 is a sectional view showing example configurations of observation optical systems of the endoscope apparatuses according to the individual embodiments of the present invention.

An observation optical system of an endoscope apparatus according to Example 6 of the present invention will now be described with reference to FIG. 12. FIG. 12 is a sectional view showing the overall configuration of the observation optical system. With the observation optical system according to this Example, it is possible to perform magnifying observation, and it is possible to perform normal observation and near-field observation by focusing in accordance with object-point distances, and thus, the configuration thereof is advantageous for observing a closer near point.

Note that the observation optical system in this Example can appropriately be combined with the illumination optical systems in the individual Examples described above.

Lens data for the observation optical system according to Example 6 are shown below. Note that Vd is the Abbe number with respect to the d-line.

| Lens Data | | | | |
|---|---|---|---|---|
| Surface Number | r | d | Nd | Vd |
| Object Surface | ∞ | d0 | | |
| 1 | ∞ | 0.36 | 1.88815 | 40.76 |
| 2 | 1.19 | 0.75 | | |
| 3 | ∞ | 0.4 | 1.523 | 65.13 |
| 4 | ∞ | 0.37 | | |
| 5 | −3.55 | 1.78 | 1.58482 | 40.75 |
| 6 | −2.38 | 0.30 | | |
| 7 | 6.83 | 0.83 | 1.51977 | 52.43 |
| 8 | −1.38 | 0.30 | 1.93429 | 18.9 |
| 9 | −2.14 | 0.05 | | |
| 10 aperture stop | ∞ | d10 | | |
| 11 | ∞ | 0.31 | 1.77621 | 49.6 |
| 12 | 1.42 | 0.58 | 1.73429 | 29.46 |
| 13 | 3.67 | d13 | | |
| 14 | 4.68 | 1.20 | 1.82017 | 46.62 |
| 15 | −6.02 | 0.03 | | |
| 16 | 4.91 | 1.60 | 1.62033 | 63.33 |
| 17 | −2.42 | 0.36 | 1.93429 | 18.9 |
| 18 | 11.2 | 0.16 | | |
| 19 | ∞ | 0.40 | 1.515 | 58.5 |
| 20 | ∞ | 0.83 | | |
| 21 | ∞ | 0.80 | 1.51825 | 64.14 |
| 22 | ∞ | 0.70 | 1.505 | 63.26 |
| 23 (Image Surface) | ∞ | | | |

| Miscellaneous Data | | |
|---|---|---|
| | Normal observation | near-field observation |
| d0 | 20 | 2.5 |
| d10 | 0.32 | 1.78 |
| d13 | 1.90 | 0.44 |
| Focal Distance | 1.19 | 1.46 |
| Maximum Image Height | 1.20 | | ft: 1.46
L: 2.1 {0094}

Example 7

Figure 13:
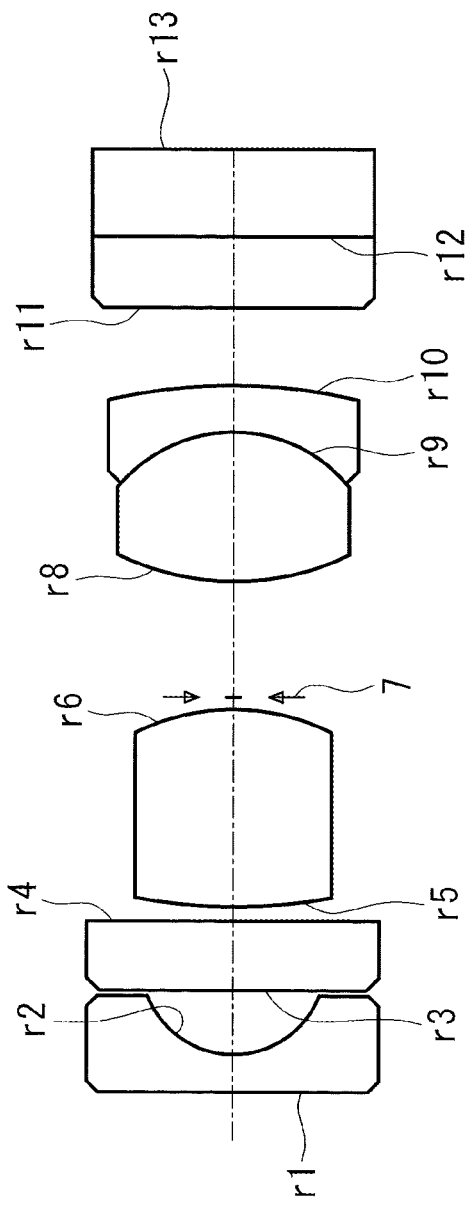
FIG. 13 is a sectional view showing example configurations of the observation optical systems of the endoscope apparatuses according to the individual embodiments of the present invention.

An observation optical system of an endoscope apparatus according to Example 7 of the present invention will now be described with reference to FIG. 13. FIG. 13 is a sectional view showing the overall configuration of the observation optical system. With the observation optical system according to this Example, although a focusing mechanism is not installed therein, it is possible to perform satisfactory near-point observation.

Note that the observation optical system in this Example can appropriately be combined with the illumination optical systems in the individual Examples described above.

Lens data for the observation optical system according to Example 7 are shown below. Note that Vd is the Abbe number with respect to the d-line.

| Lens Data | | | | |
|---|---|---|---|---|
| Surface Number | r | d | Nd | Vd |
| 1 | ∞ | 0.35 | 1.88815 | 40.76 |
| 2 | 0.916 | 0.58 | | |
| 3 | ∞ | 0.62 | 1.515 | 75.0 |
| 4 | ∞ | 0.13 | | |
| 5 | 6.689 | 1.80 | | |
| 6 | −2.028 | 0.10 | 1.74678 | 49.34 |
| 7 aperture stop | ∞ | 1.05 | | |
| 8 | 2.929 | 1.35 | 1.73234 | 54.68 |
| 9 | −1.529 | 0.42 | 1.93429 | 18.9 |
| 10 | −5.070 | 0.70 | | |
| 11 | ∞ | 0.65 | 1.51825 | 64.14 |
| 12 | ∞ | 0.80 | 1.507 | 63.26 |
| 13 Imaging Surface | | | | |

Miscellaneous Data
Object-Point Distance 20
Focal Distance 1.00
Image Height 1.02
ft: 1.0
L: 6.0

Note that the values related to the above-described conditional expressions (1) to (10) for the above-described Examples 1 to 5 are shown in Table 1, and values related to the above-described conditional expression (11) in Examples 6 and 7 are shown in Table 2.

TABLE 1

| Conditional expression | Example 1 | Example 2 | Example 3 | Example 4 | Example 5 |
|---|---|---|---|---|---|
| (1) | 3.00 | 1.67 | 1.20 | 1.67 | 3.00 |
| (2) | 0.13 | 0.10 | 0.14 | 0.10 | 0.13 |
| (3) | 0.18 | 0.17 | 0.17 | 0.17 | 0.17 |
| (4) | 1.38 | 1.70 | 1.21 | 1.70 | 1.31 |
| (5) | 1.05 | 2.18 | 1.28 | 1.17 | 1.33 |
| (6) | 6.55 | 8.88 | 5.62 | 4.77 | 5.48 |
| (7) | 4.86 | 2.32 | 3.23 | 3.46 | 4.05 |
| (8) | 1.28 | 1.76 | 1.36 | 1.18 | 1.01 |
| (9) | 0.65 | 0.42 | 0.57 | 0.92 | 1.03 |
| (10) | 1.20 | 1.36 | 1.30 | 0.92 | 0.96 |

TABLE 2

| Conditional expression | Example 6 | Example 7 |
|---|---|---|
| (11) | 0.73 | 0.16 |

{Additional Item 1}
Distances between the center of the observation optical system and the centers of the illumination optical systems satisfy conditional expression (5) below:

$$1.0 < r1/r2 < 3.0 \quad (5),$$

where r1 is the distance between the center of the observation optical system and the center of the narrow-angle illumination optical system, and r2 is the distance between the center of the observation optical system and the center of the wide-angle illumination optical system.

{Additional Item 2}

The narrow-angle illumination optical system and the wide-angle illumination optical system satisfy conditional expressions below:

$$4 < r1/|fw| < 12 \quad (6),$$

$$1 < r2/|fs| < 8 \quad (7), \text{ and}$$

$$0.8 < |fs/fw| < 2.8 \quad (8),$$

where r1 is the distance between the center of the observation optical system and the center of the narrow-angle illumination optical system, r2 is the distance between the center of the observation optical system and the center of the wide-angle illumination optical system, fs is the overall focal distance of the narrow-angle illumination optical system, and fw is the overall focal distance of the wide-angle illumination optical system.

{Additional Item 3}

The individual illumination optical systems are configured so that exiting light levels thereof satisfy conditional expression (9) below:

$$0.3 < (\varphi N \cdot fw)/(\varphi A \cdot fs) < 1.2 \quad (9),$$

where $\varphi A$ is the light-guide diameter of the narrow-angle illumination optical system, $\varphi B$ is the light-guide diameter of the wide-angle illumination optical system, fs is the overall focal distance of the narrow-angle illumination optical system, and fw is the overall focal distance of the wide-angle illumination optical system.

{Additional Item 4}

The light-guide diameters of the individual illumination optical systems satisfy conditional expression (10) below:

$$\varphi A/\varphi B > 0.8 \quad (10),$$

where $\varphi A$ is the light-guide diameter of the narrow-angle illumination optical system, and $\varphi B$ is the light-guide diameter of the wide-angle illumination optical system.

{Additional Item 5}

$$0.08 < ft/L < 1.2 \quad (11),$$

where L is the closest observation distance, and ft is the focal distance of the observation optical system when performing near-point observation.

{Additional Item 6}

The wide-angle illumination optical system is formed of three convex lenses.

The above-described embodiment leads to the following inventions.

An aspect of the present invention is an endoscope apparatus including an observation optical system that is provided at a distal end of an inserted portion of the endoscope apparatus to observe an observation subject; and a plurality of illumination optical systems that are provided in the inserted portion and that illuminate the same viewing field by distributing illumination light emitted from a light source over the observation subject, wherein, of the plurality of the illumination optical systems, the distance from the observation optical system to the widest-angle illumination optical system is smaller than the distance from the observation optical system to the narrowest-angle illumination optical system.

With this aspect, when performing near-field observation, the entire viewing-field region is irradiated with the illumination light mainly by using the widest-angle illumination optical system, and, when performing normal observation, for example, when observing far into the center portion of a lumen, the light is radiated like a spotlight by using the narrowest-angle illumination optical system, and thus, it is possible to radiate optimal illumination light in each case depending on the situations with respect to near and far illumination requirements that differ from each other.

In the above-described aspect, it is preferable that angular characteristics of the narrowest-angle illumination optical system and the widest-angle illumination optical system satisfy the conditional expression below:

$$\gamma B(60°)/\gamma A(60°) > 1 \quad (1),$$

where $\gamma A(60°)$ is an exiting-light-level ratio with respect to the center (emitting angle 0°) of the narrowest-angle illumination optical system when the emitting angle is 60°, and $\gamma B(60°)$ is an exiting-light-level ratio with respect to the center (emitting angle 0°) of the widest-angle illumination optical system when the emitting angle is 60°.

The region when the emitting angle is 60° roughly corresponds to the viewing-field region that extends to the peripheral portions of the observation region of the endoscope apparatus. Therefore, the magnitude of the exiting light level when the emitting angle is 60° becomes a determining factor of the light distribution. When the range of conditional expression (1) is exceeded, the angular characteristics of the individual illumination optical systems end up being inverted. In other words, there is a problem in that it is not possible to achieve sufficient brightness for an imaging subject at a far distance, and that the center portion becomes darker as compared with the peripheral portions when an imaging subject is at a close distance.

Because of this, by satisfying the above-described conditional expression (1), uniform illumination is achieved with the illumination light both when performing a normal observation and when performing a near-field observation, and thus, it is possible to ensure satisfactory light distribution and brightness.

In the above-described aspect, it is preferable that angular characteristics of the narrowest-angle illumination optical system and the widest-angle illumination optical system satisfy the conditional expressions below:

$$0.01 < \gamma A(50°) < 0.25 \quad (2)$$

$$0.10 < \gamma B(50°) < 0.40 \quad (3)$$

where $\gamma A(50°)$ is an exiting-light-level ratio with respect to the center (emitting angle 0°) of the narrowest-angle illumination optical system when the emitting angle is 50°, and $\gamma B(50°)$ is an exiting-light-level ratio with respect to the center (emitting angle 0°) of the widest-angle illumination optical system when the emitting angle is 50°.

The angular characteristics of the individual illumination optical system are often such that the exiting-light-level ratio of the narrow-angle illumination optical system is greater than or about equal to that of the wide-angle illumination optical system up to the emitting angle of about 0 to 30° near the center of the optical axis. However, at the emitting angle of about 50 to 60° near the center of the optical axis, the exiting-light-level ratio of the wide-angle illumination optical system is greater than that of the narrow-angle illumination optical system, and, at the emitting angle of 60°, the exiting-light-level ratio of the wide-angle illumination optical system is always greater.

Conditional expressions (2) and (3) are exiting-light-level ratios of the individual illumination optical systems at an emitting angle of 50°.

It is preferable that the angular characteristics of the wide-angle illumination optical system satisfy conditional expression (2) for the following reasons. When the lower limit of conditional expression (2) is not reached, a wide-angle light distribution cannot be achieved, and, when the upper limit of conditional expression is exceeded, although a wide-angle light distribution is achieved, it is undesirable because the center becomes dark, thus also affecting the center brightness in a distant view.

In addition, it is preferable that the angular characteristics of the narrow-angle illumination optical system satisfy conditional expression (3) for the following reasons. When the lower limit of conditional expression (3) is not reached, the angle of the light distribution becomes too narrow, which is undesirable because the brightness at the peripheral portion of the screen is also affected. In addition, when the upper limit of conditional expression (3) is exceeded, although the light distribution is improved, a decrease in the center brightness becomes problematic.

In the above-described aspect, the exiting light level of the widest-angle illumination optical system may be lower than that of the narrowest-angle illumination optical system.
{0115}
By doing so, the brightness for the distant view becomes favorable, which facilitates achieving sufficient brightness at a more-distant site, and thus, sufficient brightness can be obtained from a close-up view to a distant view.

In the above-described aspect, the exiting light level of the widest-angle illumination optical system may be greater than that of the narrowest-angle illumination optical system.

By doing so, at all object-point distances from a close-up view to a distant view, uniform and superior brightness can be achieved from the center portion of an observation-image displaying region to the most peripheral portion of the screen, which makes halation even less likely to occur, when an image is generated from an imaging-subject image. This kind of relationship is particularly suitable for a near-field-observation subject, and is suitable for an endoscope apparatus having a magnifying observation function.

REFERENCE SIGNS LIST 1 observation optical system
2A narrow-angle illumination optical system
2B wide-angle illumination optical system
5 illumination optical system
10 endoscope-inserted-portion distal-end surface

The invention claimed is:
1. An endoscope apparatus comprising:
an observation optical system that is provided at a distal end of an inserted portion of the endoscope apparatus to observe an observation subject; and
a plurality of illumination optical systems that are provided in the inserted portion and that illuminate the same viewing field by distributing illumination light emitted from a light source over the observation subject, the plurality of illumination optical systems including a widest-angle illumination optical system and a narrowest-angle illumination optical system, a light distribution of the widest-angle illumination optical system having a wider angle than light distributions of the other illumination optical systems, a light distribution of the narrowest-angle illumination optical system having a narrower angle than light distributions of the other illumination optical systems;
wherein, of the plurality of the illumination optical systems, the distance from the observation optical system to the widest-angle illumination optical system is smaller than the distance from the observation optical system to the narrowest-angle illumination optical system, and
wherein the observation optical system satisfies the conditional expression (11) below, and the each of the plurality of illumination optical systems satisfies the conditional expressions (6'), (7), and (8) below:

$$0.08 < ft/L < 1.2 \quad (11),$$

$$6 < r1/|fw| < 10 \quad (6'),$$

$$1 < r2/|fs| < 8 \quad (7), \text{ and}$$

$$0.8 < |fs/fw| < 2.8 \quad (8),$$

where L is a closest observation distance, ft is a focal distance of the observation optical system when performing near-point observation, r1 is a distance between a center of the observation optical system and a center of the narrowest-angle illumination optical system, fw is an overall focal distance of the widest-angle illumination optical system, r2 is a distance between the center of the observation optical system and a center of the widest-angle illumination optical system, and fs is an overall focal distance of the narrowest-angle illumination optical system, the closest observation distance corresponding to a distance between (a) a location of an in-focus range of an object space closest to the observation optical system and (b) a surface of the observation optical system closest to the object.

2. An endoscope apparatus according to claim 1, wherein angular characteristics of the narrowest-angle illumination optical system and the widest-angle illumination optical system satisfy the conditional expression below:

$$\gamma B(60°)/\gamma A(60°) > 1 \quad (1),$$

where $\gamma A(60°)$ is an exiting-light-level ratio with respect to the center (emitting angle 0°) of the narrowest-angle illumination optical system when the emitting angle is 60°, and $\gamma B(60°)$ is an exiting-light-level ratio with respect to the center (emitting angle 0°) of the widest-angle illumination optical system when the emitting angle is 60°.

3. An endoscope apparatus according to claim 1, wherein angular characteristics of the narrowest-angle illumination optical system and the widest-angle illumination optical system satisfy the conditional expressions below:

$$0.01 < \gamma A(50°) < 0.25 \quad (2), \text{ and}$$

$$0.10 < \gamma B(50°) < 0.40 \quad (3),$$

where $\gamma A(50°)$ is an exiting-light-level ratio with respect to the center (emitting angle 0°) of the narrowest-angle illumination optical system when the emitting angle is 50°, and $\gamma B(50°)$ is an exiting-light-level ratio with respect to the center (emitting angle 0°) of the widest-angle illumination optical system when the emitting angle is 50°.

4. An endoscope apparatus according to claim 1, wherein the exiting light level of the widest-angle illumination optical system is lower than that of the narrowest-angle illumination optical system.

5. An endoscope apparatus according to claim 1, wherein the exiting light level of the widest-angle illumination optical system is greater than that of the narrowest-angle illumination optical system.

6. An endoscope apparatus according to claim 1, wherein each of the plurality of illumination optical systems satisfies the conditional expression below:

$$1.2 < |fs/fw| < 2.2 \quad (8'),$$

where fs is the overall focal distance of the narrowest-angle illumination optical system.

7. An endoscope apparatus according to claim 1, wherein each illumination optical system includes a light guide, and wherein an exiting light level of each of the plurality of illumination optical systems satisfies the conditional expression below:

$$0.3 < (\varphi B \cdot fw)/(\varphi A \cdot fs) < 1.2 \tag{9},$$

where $\varphi A$ is a diameter of the light-guide of the narrowest-angle illumination optical system, and $\varphi B$ is a diameter of the light-guide of the widest-angle illumination optical system.

8. An endoscope apparatus according to claim 1, wherein each illumination optical system includes a light guide, and wherein an exiting light level of each of the plurality of illumination optical systems satisfies the conditional expression below:

$$\varphi A/\varphi B > 0.8 \tag{10},$$

where $\varphi A$ is a diameter of the light-guide of the narrowest-angle illumination optical system, and $\varphi B$ is a diameter of the light-guide of the widest-angle illumination optical system.

* * * * *